United States Patent [19]

Kaye

[11] Patent Number: 5,156,777
[45] Date of Patent: Oct. 20, 1992

[54] PROCESS FOR MAKING A PROSTHETIC IMPLANT

[76] Inventor: Alan H. Kaye, 435 N. Roxbury Dr., Suite 211, Beverly Hills, Calif. 90210

[21] Appl. No.: 673,027

[22] Filed: Mar. 21, 1991

[51] Int. Cl.$^5$ .................... B29C 39/02; B29C 39/44
[52] U.S. Cl. .................... 264/40.1; 264/222; 264/226; 264/227; 425/2; 623/11
[58] Field of Search .............. 264/40.1, 222, 223, 264/225, 226, 227; 425/2; 623/11

[56] References Cited

U.S. PATENT DOCUMENTS

| | | |
|---|---|---|
| 4,575,805 | 3/1986 | Moermann et al. |
| 4,611,288 | 9/1986 | Duret et al. |
| 4,742,464 | 5/1988 | Duret et al. |
| 4,752,964 | 6/1988 | Okada et al. |
| 4,790,849 | 12/1988 | Terino |
| 4,825,263 | 4/1989 | Desjardins et al. |
| 4,846,577 | 7/1989 | Grindon |
| 4,866,612 | 9/1989 | Takagi et al. |
| 4,879,668 | 11/1989 | Cline et al. |
| 4,961,154 | 10/1990 | Pomerantz et al. |

FOREIGN PATENT DOCUMENTS 0040165 11/1981 European Pat. Off.

OTHER PUBLICATIONS

Mark A. Knibbe et al., "Custom-Made Silicone Implants for Zygomaticomaxillary Augmentation", *The American Journal of Cosmetic Surgery*, vol. 8, No. 1, 1991.

*Primary Examiner*—Jan H. Silbaugh
*Assistant Examiner*—Brian J. Eastley
*Attorney, Agent, or Firm*—Spensley Horn Jubas & Lubitz

[57] ABSTRACT

A method of producing a prosthetic implant for a predetermined organ site. Three-dimensional data including surface contour information of the organ site is obtained and a physical life size model of at least a part of the surface contour of the organ site is produced based on the three-dimensional data. Thereafter, an implant model is formed onto the surface of the physical organ model, and a prosthetic implant is produced from the implant model using a casting process.

7 Claims, 2 Drawing Sheets

PROCESS FOR MAKING A PROSTHETIC IMPLANT

BACKGROUND OF THE INVENTION

1. Field of the Invention

The present invention relates to a method for making a prosthetic implant.

2. Description of Related Art

In orthopedic facial reconstructive and aesthetic surgery, a bone prosthesis may be surgically inserted between the facial skeleton and the soft tissue of the side of the patient's face to give the face a more pleasing appearance. Such bone prostheses include, for example, chin implants and malar implants. U.S. Pat. No. 4,790,849 issued Dec. 13, 1988 to Terino describes a malar implant which is positioned between the malar-zygomatic bone complex and the cheek to correct the insufficient prominence of the cheekbone. Generally, these implants are of the "off-the-shelf" type and are provided in different sizes to accommodate the normal range of patients' facial skeleton sizes. However, because these implants are of standardized shapes and sizes, and because the surface contour of the facial skeleton may differ from one individual patient to another, the implant may need to be tailored somewhat for each individual patient to form a custom fit against the surface contour of the facial skeleton of the patient during the surgical operation.

SUMMARY OF THE INVENTION

It is an object of the present invention to provide a method of making a prosthetic implant which eliminates the requirement for tailoring the prosthetic implant during the surgical implant operation It is another object of the present invention to provide a method of making a prosthetic implant which improves the fit of the implant to the surface contour of the facial skeleton of an individual patient.

These and other objects and advantages are achieved in a method for producing a prosthetic implant at a predetermined organ site, in which, in accordance with one embodiment of the present invention, three-dimensional data including surface contour information of the organ site is obtained and a physical life size model of at least a part of the surface contour of the organ site is produced based on the three-dimensional data. Thereafter, an implant model is formed on the surface of the physical organ model, and a prosthetic implant is produced from a mold formed from the implant model. In this manner, a prosthetic implant custom fit to a particular patient may be fabricated prior to surgery.

DETAILED DESCRIPTION OF THE DRAWINGS

Figure 1:
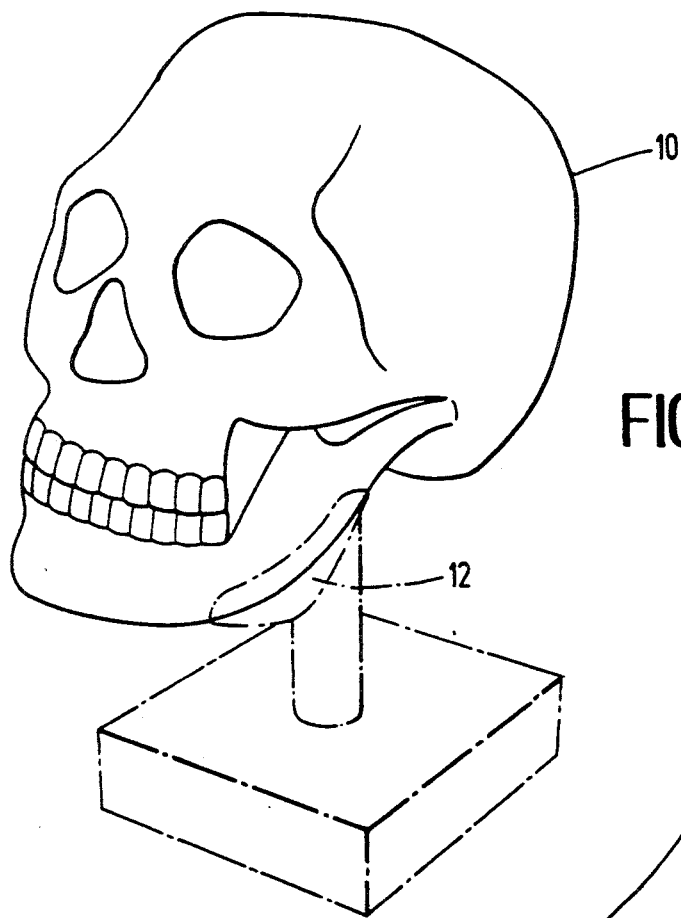
FIG. 1 is a perspective view of a physical model of the facial skeleton which is produced based on three-dimensional data obtained by computed axial tomographic (CAT) systems.
Figure 2:
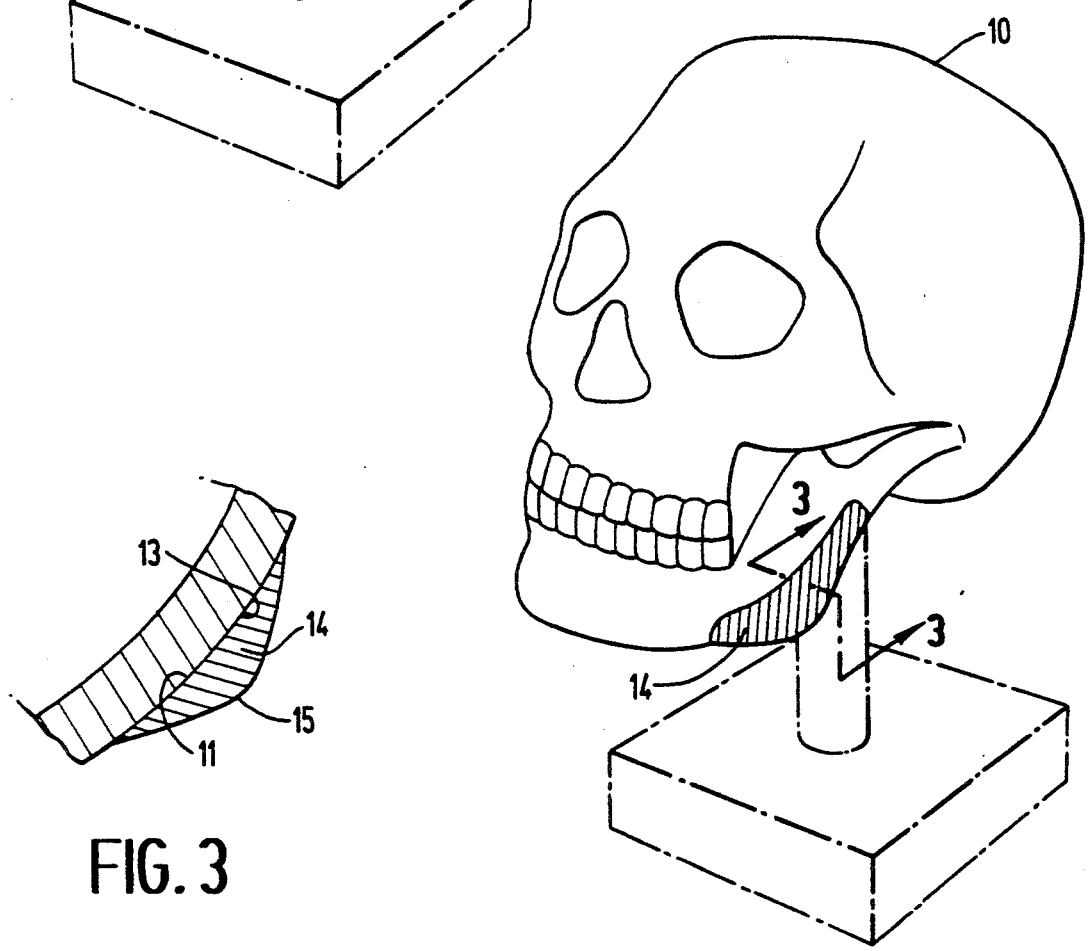
FIG. 2 is a perspective view of the physical model of the facial skeleton and a wax implant model formed onto the physical model.
Figure 4:
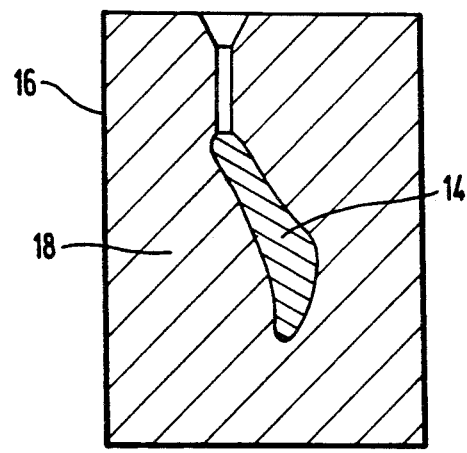
FIGS. 4-6 schematically show a lost-wax casting process for producing a custom-fit prosthetic implant.
Figure 5:
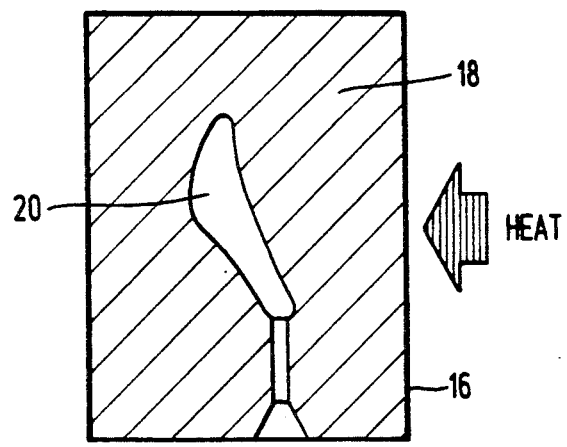
Figure 6:
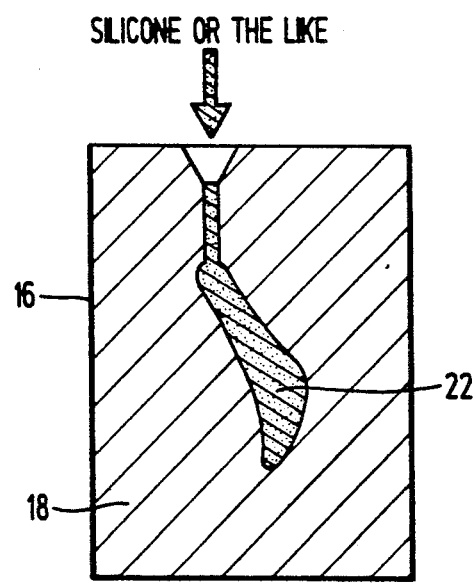

A method for producing a prosthetic implant for a determined organ site is described with reference to the accompanying drawings. In accordance with a preferred embodiment of the present invention, as illustrated in FIGS. 1 and 2, three-dimensional data including surface contour information of the patient's skull is obtained and a physical model of the skull 10 is produced based on the three-dimensional data. Thereafter, a wax implant model 14 is formed on the surface of the physical organ model 10. A prosthetic implant 22 is then produced using a lost-wax casting method as generally illustrated in FIGS. 4-6.

Computed axial tomographic (CAT) systems may be used according to the present invention to produce three dimensional data representative of the facial skeleton of a patient or any other desired organ site. For example, U.S. Pat. No. 4,879,668 describes a CAT system which is capable of displaying selected internal surface structures of a three-dimensional body and is also capable of graphically peeling away selected tissue surfaces from three-dimensional images of internal surface structures. In one aspect of the present invention, three-dimensional data including surface contour information of the skull of the patient is generated by a CAT system (not shown). Such data may preferably include surface contour information of the patient's entire skull. However, it is also appreciated that the data may be limited to a part of the patient's skull, such as, for example, the facial skeleton, or even only the malar-zygomatic or chin regions depending upon the surgical requirements.

In a further feature of the present invention, the three-dimensional data generated by the CAT system is used to generate a physical model of the desired organ site, such as the skull of the patient. Typically, the CAT generated three dimensional data may be used to operate a numerically controlled machine tool (not shown) to fabricate a three-dimensional physical model. For example, similar methods and apparatus are described in detail in U.S. Pat. No. 4,742,464 issued May 3, 1988 to Duret et al and U.S. Pat. No. 4,575,805 issued Mar. 11, 1986 to Moermann et al.

Figure 3:
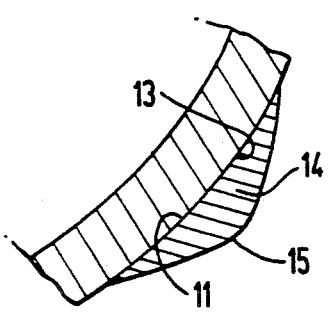
FIG. 3 is a cross-sectional view taken along the line 3-3 of FIG. 2.

FIG. 1 illustrates the physical model of the patient's skull 10 which is fabricated preferably in life-size utilizing the CAT generated three dimensional data. The mandible of the skull model 10 has an area indicated in a dash-and-dotted line 12, which requires the implantation of a prothesis. Referring to FIG. 2, the wax implant model 14 is applied directly to the physical model 10 at the area 12 so that the inner surface 11 of the wax implant 14 conforms to the surface contour 13 of the area 12. Since the life size physical model 10 has a very faithful representation of the surface contour of the patient's facial skeleton at area 12, the wax implant inner surface 11 as a result is highly complementary to the actual external surface contour 13 of the area 12 as shown in FIG. 3. Also, the external surface 15 of the wax implant model 14 is readily shaped to mimic the normal anatomy of the facial skeleton or to provide a pleasing aesthetic shape.

FIGS. 4-6 show a typical lost wax method for making a custom fit prosthetic implant in accordance with the present invention. Referring to FIG. 4, the wax implant model 14 is carefully removed from the skull model 10 and is placed in a coating cylinder 16 which is filled with a molding material to form a mold 18. After the mold 18 has hardened, the coating cylinder 16 is heated to melt and sublimate the wax implant model 14 thereby forming a cavity 20 as shown in FIG. 5. A solid biologically inert, pliant, flexible and compressible material such as a silicone rubber is then poured or injected into the cavity 20 to fabricate a malar prosthetic implant 22 as shown in FIG. 6.

The mold 18 may be formed in two symmetrical halves which can be separated to facilitate removal of the wax after the cavity has been formed. The wax is typically removed by scraping or may be boiled out with hot water. The implant material is then placed inside the mold and the mold halves are reassembled and closed under pressure. After curing, the mold is opened and the implant is removed.

It should be appreciated that the prosthetic implant 22 is a substantially exact duplicate of the wax implant model 14. Therefore the inner surface of the implant 22 precisely complements the external surface contour 13 at the area 12 of the actual mandible of the patient, and the external surface of the implant 20 defines a tailored contour which mimics the normal anatomy of the facial skeleton or has a more pleasing aesthetic shape than that provided by nature. As a result, the method in accordance with the present invention provides a prosthetic implant which precisely fits the surface contour of an organ site of an individual patient and thereby substantially or totally eliminates the need for tailoring the prosthetic implant during the surgical procedure.

The present invention has been so far described with particular reference to facial prosthetic implants. However, modifications of the present invention in its various aspects will be apparent to those skilled in the art. For example, it should be appreciated that the method of making a prosthetic implant in accordance with the present invention is applicable to reconstructive and aesthetic surgery of other organ sites including "soft organs". Also, other methods of scanning the patient to obtain the three-dimensional data may be used as well as other skeletal model making processes and mold making processes. As such, the scope of the invention is not limited to the particular embodiments herein described but extends to all modifications, embodiments, alternatives and equivalents falling within the scope of the appended claims.

What I claim is:

1. A method for producing a prosthetic implant for a predetermined organ site comprising the steps of:
    scanning an organ site and obtaining three-dimensional scan data representing the surface contours of the organ site;
    producing a physical life size model of at least a part of the surface contour of the organ site based on the scan data;
    forming an implant model on the surface of the physical organ model;
    casting a mold using the implant model; and
    producing a prosthetic implant from the implant model mold.

2. A method for producing a prosthetic implant for a determined organ site comprising the steps of:
    obtaining three-dimensional CAT scan data which represents surface contour information of the organ site;
    producing a physical life size model of at least a part of the surface contour of the organ site based on the CAT scan data;
    forming a wax implant model on the surface of the physical organ model; and
    producing a prosthetic implant using a lost-wax casting process.

3. The method for producing a prosthetic implant for a determined organ site according to claim 2 wherein said step of producing a prosthetic implant comprises placing the wax implant model in a coating cylinder to form a mold, heating the mold to sublimate the wax thereby creating a cavity in the mold in the shape of the wax implant model, and placing a compliant material in the cavity of the coating cylinder to form the prosthetic implant.

4. The method for producing a prosthetic implant for a determined organ site according to claim 3 wherein said compliant material is silicone.

5. A method for producing a prosthetic implant to be adapted to a predetermined internal organ site covered with soft tissue, comprising the steps of:
    producing a full scale model of the surface contour of the organ site beneath the soft tissue;
    forming an implant model onto the surface of the full scale organ model; and
    producing a prosthetic implant using the implant model in a casting process.

6. The method for producing a prosthetic implant according to claim 5 wherein said step of producing a full scale model includes scanning the organ site by a computed axial tomographic system to obtain information defining the surface contour of the organ site, and producing the full scale model of the organ site based on the surface contour information using a numerically controlled machine tool.

7. The method for producing a prosthetic implant according to claim 5 wherein said step of producing a prosthetic implant includes placing the wax implant model in a coating cylinder, heating the coating cylinder to sublimate the wax thereby creating a cavity in the shape of the wax implant model, and placing a compliant material in the cavity of the coating cylinder.

* * * * *